United States Patent [19]
Murray

[11] 3,957,436
[45] May 18, 1976

[54] RESULTANT COLOR STEP INDICATOR

[75] Inventor: Dennis M. Murray, Golden Valley, Minn.

[73] Assignee: Kallestad Laboratories, Inc., Chaska, Minn.

[22] Filed: Apr. 29, 1974

[21] Appl. No.: 464,986

[52] U.S. Cl. ............................ 23/230 R; 23/230 B; 23/230.3; 116/114 AM
[51] Int. Cl.$^2$ ........................G01N 31/22; G01N 33/16
[58] Field of Search .......... 23/230 R, 230 B, 230 A, 23/230.3; 208/12; 44/59 (U.S. only); 116/114 R (U.S. only), 114 AM; 73/432 R (U.S. only)

[56] References Cited
UNITED STATES PATENTS

| | | | |
|---|---|---|---|
| 2,061,500 | 11/1936 | Brewer | 116/114 R X |
| 2,925,333 | 2/1960 | Thompson | 44/59 |
| 3,062,963 | 11/1962 | Douty | 23/230 R X |
| 3,483,735 | 12/1969 | Packo | 23/230 R X |
| 3,733,178 | 5/1973 | Eriksen | 23/230 B |
| 3,862,120 | 1/1975 | Orelup | 23/230 R X |

*Primary Examiner*—Joseph Scovronek
*Attorney, Agent, or Firm*—Dorsey, Marquart, Windhorst, West & Halladay

[57] ABSTRACT

A resultant color step indicator for use in various diagnostic or analytic test procedures particularly useful in those involving qualitative and quantitative analysis, such as radioimmunoassay, where a number of steps must be accomplished consecutively in order to get a proper final measurement. The various reagents which must be consecutively added are colored with an inert coloring. The coloring does not enter into the chemical reaction that yields the test results. It serves only to combine or intermix with the other coloring to indicate which steps have been completed. As the test is run, each step in the procedure which involves the addition of a different colored reagent results in a color change in the test specimen and the resultant color of the test specimen indicates which steps in the procedure have been accomplished.

10 Claims, 2 Drawing Figures

HGH FLOW CHART

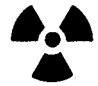

| Steps of Procedure | Reagent Color | Background | Tube O | Tubes A-E | Patient Sample |
|---|---|---|---|---|---|
| HGH Buffer (ml) | | 0.20 | 0.20 | 0.10 | 0.10 |
| HGH Standards (ml) | | — | — | 0.10 | — |
| Patient Sample (ml) | | — | — | — | 0.10 |
| Antiserum to HGH (ml) | ▨ | — | 0.10 | 0.10 | 0.10 |
| Incubate 2 hrs. at 37°C | | — | ▨ | ▨ | ▨ |
| $^{125}$I-HGH (ml) | ▨ | 0.50 | 0.50 | 0.50 | 0.50 |
| Incubate 1 hr. at 37°C | | ▨ | ▨ | ▨ | ▨ |
| Precipitating Antiserum (ml) | ▨ | 0.20 | 0.20 | 0.20 | 0.20 |
| Incubate 2 hrs. at 37°C | | ▨ | ▨ | ▨ | ▨ |
| Centrifuge at 3000 x g at 4°C | | 30 min. | 30 min. | 30 min. | 30 min. |

IgE FLOW CHART 

| Steps of Procedure | Reagent Color | Background | Tube 0 | Tubes A-E | Patient Sample |
|---|---|---|---|---|---|
| IgE Buffer (ml) | | 0.5 | 0.5 | 0.5 | 0.5 |
| IgE Standards (ml) | | — | — | 0.1 | — |
| Patient Sample (ml) | | — | — | — | 0.1 |
| $^{125}$I-IgE (ml) | | 0.1 | 0.1 | 0.1 | 0.1 |
| Color after Addition of $^{125}$I-IgE | | | | | |
| Antiserum to IgE (ml) | | — | 0.1 | 0.1 | 0.1 |
| Incubate Overnight at Room Temp | | | | | |
| Precipitating Antiserum (ml) | | 0.5 | 0.5 | 0.5 | 0.5 |
| Rotate 2 hours at Room Temp. | | | | | |
| Centrifuge at 3700 x g at 4°C | | 2 min. | 2 min. | 2 min. | 2 min. |
| Centrifuge at 3700 x g at 4°C | | 30 min. | 30 min. | 30 min. | 30 min. |
| IgE Buffer (ml) | | 1.0 | 1.0 | 1.0 | 1.0 |
| Centrifuge at 3700 x g at 4°C | | 30 min. | 30 min. | 30 min. | 30 min. |

*Fig. 2*

HGH FLOW CHART 

| Steps of Procedure | Reagent Color | Background | Tube 0 | Tubes A-E | Patient Sample |
|---|---|---|---|---|---|
| HGH Buffer (ml) | | 0.20 | 0.20 | 0.10 | 0.10 |
| HGH Standards (ml) | | — | — | 0.10 | — |
| Patient Sample (ml) | | — | — | — | 0.10 |
| Antiserum to HGH (ml) | | — | 0.10 | 0.10 | 0.10 |
| Incubate 2 hrs. at 37°C | | — | | | |
| $^{125}$I-HGH (ml) | | 0.50 | 0.50 | 0.50 | 0.50 |
| Incubate 1 hr. at 37°C | | | | | |
| Precipitating Antiserum (ml) | | 0.20 | 0.20 | 0.20 | 0.20 |
| Incubate 2 hrs. at 37°C | | | | | |
| Centrifuge at 3000 x g at 4°C | | 30 min. | 30 min. | 30 min. | 30 min. |

*Fig. 1*

RESULTANT COLOR STEP INDICATOR

BACKGROUND OF THE INVENTION

The field of art of the present invention includes various diagnostic or analytic test procedures such as those involving qualitative and quantitative analysis in which a number of steps must be consecutively performed in order to get a proper final measurement. An exemplary test procedure of this type is radioimmunoassay where very small volumetric additions of various reagents, on the order of 100 microliters, must be added to standard dilutions of a patient's sample to determine the presence and quantity of certain proteins such as growth hormone, or immunoglobulins associated with allergic reactions or parasitic infections. Prior to immunoassay two of the methods for measuring small quantities of materials were bioassays and radial diffusion.

As explained more fully in an article entitled "Principles of Radioimmunoassay" written by Dr. James McQuire (48 Mayo Clin. Proc. at 637, Sept., 1973), radioimmunoassay provides a method for measurement of small quantities of substances not measurable by other techniques. The techniques of immunoassay have been applied to a number of substances of various structures. The technique evolved from work with the insulin system: insulin resistance was being investigated, antibodies to insulin were identified, then antibodies to insulin were subsequently produced, and a method was developed whereby very small quantities of insulin could be measured by application of these antibodies. These techniques have now been applied to a wide variety of both large and small, principally organic, molecules.

In a radioimmunoassay, antibodies to the substance being measured are necessary. These are generally produced by hyperimmunization of experimental animals. In addition, the antibodies must have high affinity for the substance being measured.

Besides the antibody of high affinity, a radiolabeled detector substance is utilized. The antibody molecules need not be specific if the detector is specific; therefore, it is possible to immunize with rather crude materials. Some radiolabeled materials currently used are tagged with either $^{131}I$, $^{125}I$, or $^{3}H$. The radiolabeled substance must be pure, and there must be a standard to make comparisons. The major requisite necessary in the radioimmunoassay system is a method of separating antibody-free radioactivity from antibody-bound radioactivity.

In the radioimmunoassay procedure, the concentrations of antibody and of radioactive labeled material in the tube are kept constant. A standard curve is prepared by using known amounts of the substance to be measured. The ordinate value can be expressed in a variety of ways, as percent precipitated or bound: free ratio (B/F) or any expression of these themes. There is a relationship between the amount of unlabeled material which was in the tube and the amount of proportion of radioactivity which is precipitated. This standard curve, therefore, permits one to determine the amount of the selected protein in an unknown sample from knowing the percent of radioactivity precipitated.

In the prior art procedure it was necessary for the technician running the procedure to either keep records to indicate where he or she was in the procedure or to run the test procedure in one session which, very often, ran 5 hours or more. However, often in running such a test procedure the technician was interrupted or for some other reason lost track of where he or she was in the procedure. The present invention is designed to eliminate that problem.

SUMMARY OF THE INVENTION

There are, of course, a number of tests, in qualitative analysis particularly, in which a color change indicates the presence of a certain element. This is not an object of the present invention.

The present invention alleviates the problem of record keeping or constant monitoring during test procedures wherein small volumetric additions are made to a solution. Small additions normally do not result in a sufficient volumetric change so that the technician can conveniently and readily observe where in the test procedure he or she was prior to being interrupted.

In this invention the various reagents utilized are colored with an inert coloring. The coloring does not enter into the chemical reaction that yields the test results and thus, in the present invention, the color does not indicate the presence or absence of any particular element. It indicates only what steps in the procedure have been done. Since the reagents are color coded as the test is run, every step in the procedure results in a color change eliminating incorrect additions. Technologists can resume a procedure where it was terminated after unscheduled (but many times necessary) interruptions without fear of duplicating or skipping steps.

The invention thus resides in color coding with an inert color or pigment at least one substance of a plurality of substances which are to be mixed or added together in a multi-step chemical process.

It is therefore an object of the present invention to provide a means for determining, by the resultant color of a sample utilized in qualitative or quantitative analysis, the precise step or steps which have been accomplished previously in the procedure.

It is a further object of the present invention to provide an alternative to record keeping or the memory of the technician who performs a multiple step procedure in qualitative or quantitative analysis so that interrupted procedures may be resumed without fear of duplicating or skipping steps in the procedure.

These and other objects of the present invention will become apparent to those skilled in the art upon consideration of the accompanying specification, drawing and claims.

DESCRIPTION OF THE DRAWING

FIG. 1 is a flow chart of a procedure utilized to detect human growth hormone wherein the reagents are color coded in accordance with my invention so that the resultant color of the test specimens and samples indicate which steps in the procedure have been accomplished.

FIG. 2 is a flow chart of a procedure utilized to detect immunoglobulin E wherein the reagents are color coded in accordance with my invention so that the resultant color of the test specimens and samples indicate which steps in the procedure have been accomplished.

DESCRIPTION OF THE PREFERRED EMBODIMENTS

It will be understood by those skilled in the art that the present invention may be utilized with many diagnostic or analytic test procedures, such as qualitative and quantitative analysis, in which there are a number of steps which must be done consecutively in order to get a proper final measurement. One procedure to which the invention has been successfully applied is radioimmunoassay utilized to detect growth hormone levels in human plasma which is clinically significant to verify suspected Hypopituitarism or suspected Acromegaly. A similar analysis, as described more fully below, may be utilized to detect a human immunoglobulins such as those associated with allergen E. High immunoglobulin E (IgE) serum levels have been observed in patients suffering allergic diseases such as asthma, hay fever, allergic rhinitis, atopic eczema and in the Wiskott-Aldrich syndrome.

As indicated more fully below, the test procedures for these analyses are very complicated due to the low concentration of proteins to be detected and involve steps in the procedure wherein very small volumetric additions are made throughout the procedure, on the order of 100 microliters. Thus, previous additions are not readily apparent from observance of volumetric changes in the sample being tested. In addition, the various steps in the procedures do not require the technician's constant presence, for example, when the test tubes are incubated for a number of hours or overnight or when the tubes are placed in a centrifuge for ½ an hour or more. Since many procedures require repeated additions and incubation periods after each addition, the technician may not remember at what stage in the procedure the testing was left and thus is required to guess or to start over. It is also common while running a test procedure that the technician is interrupted or for some other reason loses track of where he or she is in the procedure. The present invention is designed to eliminate these problems in addition to providing a means for making best use of a technician's time. Since the present invention conclusively indicates the precise stage of the test, which steps have been accomplished and which have not, the technician may perform other tests while his or her presence is not required for a test which utilizes the present invention.

As demonstrated below, to eliminate the problems outlined above, the present invention utilizes reagents which are colored with an inert coloring. The coloring does not enter into the chemical reaction that yields the test results. It serves only to combine or intermix with previously added coloring so that the resultant color of the sample or solution upon which the test is being run will specifically and conclusively indicate which steps have been completed. It has been found that commercially prepared food coloring, such as that prepared by the Durkee Company, is suitable for the purposes of the invention. As a further aid to the technician, and in accordance with the present invention, color coded flow charts may also be prepared such as shown in FIGS. 1 and 2 for convenient reference by the technician.

The procedure for detecting human growth hormone (HGH) with a radioimmunoassay procedure, utilizing the invention, is as follows:

To perform the procedure the following materials are necessary. Five vials of lyophilized HGH Standards. The Standards may be calibrated using the Human Growth Hormone Primary Reference (No. 1652 C) from the National Pituitary Agency under programs supported by the National Institute of Arthritis and Metabolic Diseases in Bethesda, Maryland. These Standards are utilized to create a standard curve which must be established for each run of unknowns.

The Standards should be run in duplicate and average values used in construction of a standard curve. For simplicity, although described separately, procedures for the Standards and patients' samples should be run simultaneously.

Since the radiolabeled material is tagged with $^{125}I$, at the conclusion of the test the radioactivity of each of the Standards is counted with a gamma counter to construct the standard curve. The reading from the patient's sample is then compared to the standard curve to obtain the HGH concentration in the sample being tested. It should be understood that while five points on the standard curve are recommended it would be possible with a much greater percentage of error to construct a standard curve of only two points.

In addition to the HGH Standards, the test procedure requires one vial of HGH Buffer 8 milliliters) and three additional vials of reagents. The additional vials would be a vial of $^{125}I$-HGH, lyophilized, to which the color blue has been added, one vial of antiserum to HGH, lyophilized, to which the color yellow has been added, and one vial of precipitating antiserum, lyophilized, to which the color red has been added. The reagents are prepared in a conventional manner and thereafter the steps for analysis of the patients' samples, based on the Standards, would be as follows:

A standard curve must be established for each run of unknowns. Standards should be run in duplicate and average values used in construction of the standard curve. For simplicity, procedures for standards and patient samples are run simultaneously. The color coded flow chart of FIG. 1 may be used as an abbreviated guide for the procedure.

STEP 1. Duplicate sets of tubes should be labeled A, B, C, D, E, O and Bkg. (Background).

STEP 2. One hundred microliters of HGH Buffer should be added to tubes A, B, C, D and E and 200 microliters of HGH Buffer should be added to tubes O and Bkg.

STEP 3. The HGH Standards should be added to the appropriately labeled tubes in the following manner:
Tubes A — 100 microliters of Standard A
Tubes B — 100 microliters of Standard B
Tubes C — 100 microliters of Standard C
Tubes D — 100 microliters of Standard D
Tubes E — 100 microliters of Standard E STEP 4. One hundred microliters of Antiserum to HGH (yellow) should be added to all tubes except Bkg. and mixed by gently swirling.

At this stage in the procedure, as indicated in FIG. 1, all tubes would be yellow in color except the tube labeled "Bkg." which would be clear. The resultant colors would therefore indicate that the first four steps had been accomplished and the remaining steps had not.

STEP 5. All tubes should be sealed, with stoppers, and incubated at 37° for 2 hours.

STEP 6. Five hundred microliters of $^{125}I$-HGH (blue) should be added to all tubes and mixed by gently swirling.

As indicated in FIG. 1, at this stage in the procedure the appearance or color of the solution in each of the tubes would be green except the tube labeled "Bkg." which would be blue in color. The resultant colors would indicate that the first six steps had been accomplished and the remaining steps had not.

STEP 7. All tubes should again be sealed and incubated at 37°C for 1 hour.

STEP 8. Two hundred microliters of Precipitating Antiserum (red) should be added to all tubes.

After STEP 8 the appearance or resultant color of the solution in each of the tubes would be brown, except the tube labeled "Bkg." which would be violet in color. As shown in FIG. 1, this would indicate that all additions had been made and that none had been skipped. It would thus indicate that all of the mixing steps had been accomplished.

STEP 9. All tubes should be mixed by gently swirling and sealed with stoppers.

STEP 10. All tubes should be incubated at 37°C for 2 hours.

STEP 11. Centrifuge all tubes at 1800 RCF for 30 minutes or equivalent.

STEP 12. The supernatant from all tubes should be poured off.

STEP 13. The tubes should be inverted for 5 minutes on absorbent paper.

STEP 14. The radioactivity of all tubes should be counted with a gamma counter for 1 to 2 minutes. Lower efficiency counters may require longer counting times for precision.

All patients' samples should be run in duplicate and the average value used in the calculations. The procedure for the patients' samples is identical to that described above for the Standards except that for STEP 1 a set of duplicate tubes for each patient's sample is labeled including sample identification and dilution factor and for STEP 3 100 microliters of patient serum is added to the appropriately labeled tubes.

It should be noted that after each step in the procedure where a reagent is added the resultant color of each of the tubes is varied. The possibility of error due to the technician skipping a step or repeating a step is virtually eliminated because the resultant color of each of the tubes conclusively shows which reagents have been previously added during the test procedure.

After the procedure has been completed the standard curves are constructed by utilizing the gamma counter to count the radioactivity of each of the tubes, including background, and the counts are corrected by subtracting the background count. The corrected results of each of tubes A through E are ratioed to the corrected count from tube O and are plotted on 3 cycle semi logarithmic graph paper. The patient's sample is also ratioed to the corrected count in tube O and the HGH concentration in the patient's sample is determined from the intersection of the reading with the standard curve in a conventional manner.

The use of a different order of colors, and in a longer procedure, is demonstrated in FIG. 2 which charts a procedure wherein the invention may similarly be utilized to determine levels of Immunoglobulin E (IgE). This assay is a modification of the double antibody method and is an overnight procedure which utilizes the following materials: five vials of IgE Standards (A, B, C, D and E), lyophilized, which are calibrated against Reference Pool II IgE from the NCI Immunoglobulin Reference Center in Springfield, Virginia; one vial of $^{125}$I-IgE, lyophilized, blue in color; one vial of Antiserum to IgE, lyophilized, yellow in color; one vial of Precipitating Antiserum, 20 milliliters, red in color; and two vials of IgE Buffer, 45 milliliters per vial.

Thereafter, the procedure is similar to that outlined above for a determination of HGH except for the quantities added, time factors, and the effect of the intermixing of the colors on the resultant color.

As indicated above, duplicate sets of tubes should be labeled A, B, C, D, E, O and Bkg. (Background) and one set of duplicate tubes should be labeled for each patient's sample indicating that dilution factor and identification of the sample. For this procedure a one to ten dilution of each patient's serum should be prepared to decrease the concentration of protein using the IgE Buffer as a diluent. Five hundred microliters of the IgE Buffer should be added to all tubes. One hundred microliters of the Standards (A—E) should be added to the appropriate tubes A — E and 100 microliters of the diluted serum for each of the patients should be added to the appropriately labeled patients' tubes. One hundred microliters of $^{125}$I-IgE (blue) should then be added to all tubes and mixed by gently swirling.

The appearance of all tubes will now be blue indicating that the radiolabeled IgE has been added.

One hundred microliters of Antiserum to IgE (yellow) should be added to all tubes except Bkg., and mixed by gently swirling.

As shown in FIG. 2, the resultant color of the solution in each of the tubes would be green except for the tube labeled "Bkg." which would remain blue. This color pattern would indicate to the technician that both the radiolabeled IgE and the Antiserum to IgE had already been added but that the Precipitating Antiserum had not, as yet, been added.

All of the tubes should then be incubated overnight at room temperature and the next morning 500 microliters of Precipitating Antiserum (red) should be added to all tubes.

The addition of the Precipitating Antiserum would turn the solution in the tube labeled "Bkg." violet and the resultant color in the remaining tubes would be brown. This would indicate to the technician that all steps involving the addition of a reagent had been accomplished and that none had been skipped.

The balance of the procedure is conventionally performed and involves capping the tubes, rotating them at room temperature and centrifuging them for 2 minutes with the caps and 30 minutes without the caps. Thereafter, the supernatant is removed from all tubes, 1 milliliter of IgE Buffer is added and the precipitate is resuspended. The tubes are centrifuged again for 30 minutes and the supernatant is removed for counting with the gamma counter to create the standard curve to determine the IgE concentration in the patients' samples.

As noted throughout the procedures outlined above, the appearance of each of the tubes conclusively indicates which step in the procedure has been accomplished. The intermixing of the colors of the reagents creates a resultant color in the Standards or samples, and in the background, which demonstrates the precise additions which have previously been made and indicates which addition must be made next to continue or complete the procedure. This convenient control may be even further simplified for any adaptable procedure by the creation of flow charts which are color coded in the manner of FIGS. 1 and 2.

Having thus described my invention it should be obvious that my invention may be adapted conve- niently to many such diagnostic or analytic procedures, particularly those involving qualitative and quantitative analyses where there are a number of steps which must be performed consecutively to obtain the proper final result or measurement. My invention is adaptable to being utilized with these procedures and each of these procedures are within the intendment of my invention.

Having thus described my invention I claim as follows.

1. In a chemical process wherein a plurality of substances are to be mixed with a test substance in a sequence of discrete steps, the improvement comprising:
   color coding 2 or more of the plurality of substances, each with a different inert color; and
   sequentially mixing each of the plurality of substances with the test substance and any substances mixed with the test substance in previous steps, so that the addition of each color coded substance is effective to change the cumulative color of the previously mixed substances in an identifiable manner whereby the resultant color of the mixture after each addition of a color coded substance is a conclusive indication that the step of adding the color coded substance has been completed.

2. The chemical process of claim 1 wherein the plurality of substances to be added are in liquid form and wherein the substances are color coded with inert pigments which are in solution with the substances.

3. The chemical process of claim 1 wherein the plurality of substances to be added are reagents which are to be sequentially added to a liquid test solution and further comprising the step of color coding each of the reagents prior to their addition to the solution with different inert colors so that the sequential adding of each of the reagents to the solution causes the resultant color of the solution to change after each addition, thereby indicating the addition of each such reagent.

4. The chemical process of claim 3 wherein the process is an analytic test procedure wherein a plurality of reagents are sequentially added to the solution and wherein each reagent is color coded, each with a different inert pigment.

5. The chemical process of claim 1 wherein the process is radioimmunoassay wherein some of the plurality of substances to be added are liquid reagents which are consecutively added during the process to form a solution and wherein two or more of the reagents are color coded.

6. The chemical process of claim 5 wherein the process is HGH radioimmunoassay and wherein three reagents are sequentially added to the solution each of which is color coded with a different color.

7. The chemical process of claim 6 wherein the first of the three reagents to be added to the solution is colored blue, the second of the reagents to be added is colored yellow and the third of the reagents is colored red.

8. The chemical process of claim 5 wherein the process is IgE radioimmunoassay and wherein three reagents are sequentially added to the solution each of which is color coded with a different color.

9. The chemical process of claim 8 wherein the first of the three reagents to be added to the solution is colored yellow, the second of the reagents to be added is colored blue and the third of the reagents is colored red.

10. The chemical process of claim 1 wherein the improvement further comprises color coding all of the plurality of substances, each with a different inert color, whereby the resultant color of the mixture after each addition is a conclusive indication that each step in the process has been completed.

* * * * *